United States Patent [19]

Krapcho et al.

[11] 3,994,880

[45] Nov. 30, 1976

[54] 2,3,3A,4,6,7-HEXAHYDRO-2-HETEROCYCLICALKYL-3-ARYL-7-(ARYLMETHYLENE)THIOPYRANO[4,3-C]PYRAZOLES AND ANALOGS THEREOF

[75] Inventors: John Krapcho, Somerset; Chester F. Turk, Kendall Park; George C. Rovnyak, Hopewell, all of N.J.

[73] Assignee: E. R. Squibb & Sons, Inc., Princeton, N.J.

[22] Filed: Apr. 21, 1976

[21] Appl. No.: 678,852

[52] U.S. Cl. .................... 260/240 F; 260/293.57; 260/247.1 L; 260/268 BC
[51] Int. Cl.² ............... C07D 409/06; C07D 495/04
[58] Field of Search.................... 260/240 F

[56]  References Cited
UNITED STATES PATENTS

| 3,897,420 | 7/1975 | Krapcho et al. | 260/240 F |
| 3,962,222 | 6/1976 | Krapcho et al. | 260/240 F |

*Primary Examiner*—Allen B. Curtis
*Attorney, Agent, or Firm*—Lawrence S. Levinson; Merle J. Smith; Donald J. Barrack

[57]  ABSTRACT

Anti-inflammatory activity is exhibited by compounds having the formula

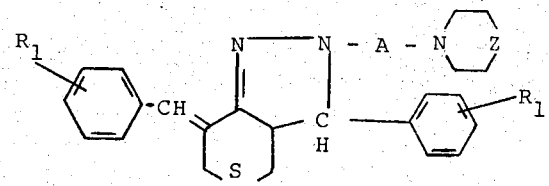

the salts thereof, and the 5-oxide and 5,5-dioxide thereof, wherein A is a straight or branched chain alkylene group; $R_1$ is hydrogen, alkyl, alkoxy, trifluoromethyl, halogen, nitro, dialkylamino, or alkylsulfinyl; and Z is $CH_2$, oxygen or $N-R_2$, wherein $R_2$ is hydrogen, alkyl, aryl, or arylalkyl.

14 Claims, No Drawings

2,3,3A,4,6,7-HEXAHYDRO-2-HETEROCYCLICALKYL-3-ARYL-7-(ARYLMETHYLENE)THIOPYRANO[4,3-C]PYRAZOLES AND ANALOGS THEREOF

BRIEF DESCRIPTION OF THE INVENTION

Compounds having the formula

I the 5-oxide and 5,5-dioxide thereof, and the pharmaceutically acceptable acid addition salts thereof, have useful pharmacological activity, and can be used in mammals to treat inflammation. In formula I, and throughout the specification, the symbols are as defined below.

A can be a straight or branched chain alkylene group having 2 to 5 carbon atoms; and $R_1$ can be hydrogen, alkyl, alkoxy, trifluoromethyl, halogen, nitro, dialkylamino, or alkylsulfinyl;

Z can be $CH_2$, oxygen or $N-R_2$, wherein $R_2$ is hydrogen, alkyl, aryl, or arylalkyl.

The terms alkyl and alkoxy, as used throughout the specification (by themselves or as part of a larger group) refer to groups having 1 to 8 carbon atoms. Alkyl and alkoxy groups having 1 to 3 carbon atoms are preferred.

The term aryl, as used throughout the specification (by itself or as part of a larger group) refers to phenyl or phenyl substituted with an alkyl, alkoxy, or halogen group. Phenyl is the preferred aryl group.

The term halogen, as used throughout the specification, refers to fluorine, chlorine, bromine, and iodine; fluorine and chlorine are preferred.

DETAILED DESCRIPTION OF THE INVENTION

The compounds of formula I (and the 5-oxides and 5,5-dioxides thereof) are prepared using as starting materials a substituted tetrahydro-4H-thiopyran-4-one having the formula

II or a 1-oxide or 1,1-dioxide thereof, and a hydrazine having the formula

III $\quad H_2NNH-A-N\overset{\frown}{\underset{\smile}{}}Z$.

The compounds of formulas II and III are readily obtainable; see, for example, *Journal of the American Chemical Society*, 79:156 (1957) and *Journal of Medicinal Chemistry*, 7:493 (1964).

A substituted tetrahydro-4H-thiopyran-4-one of formula II can be prepared by reacting tetrahydro-4H-thiopyran-4-one with an appropriate benzaldehyde having the formula

IV

The corresponding 1-oxide or 1,1-dioxide can be prepared by reacting a substituted tetrahydro-4H-thiopyran-4-one of formula II with an appropriate amount of an oxidizing agent; sodium periodate is preferred for preparing a 1-oxide and hydrogen peroxide is preferred for preparing a 1,1-dioxide.

A hydrazine of formula III can be prepared by reacting an excess of hydrazine ($H_2NNH_2$) with a haloamine having the formula V $\quad X-A-N\overset{\frown}{\underset{\smile}{}}Z$, wherein X is chlorine or bromine.

Reaction of a substituted tetrahydro-4H-thiopyran-4-one of formula II (or a 1-oxide or 1,1-dioxide thereof) with a hydrazine of formula III yields a product of formula I, or the corresponding 5-oxide or 5,5-dioxide. The reaction can be run in an organic solvent, preferably a lower alkanol such as methanol. While reaction conditions are not critical, the reaction will preferably be run at, or near, the reflux temperature of the solvent.

Alternatively, the compounds of formula I can be obtained by first reacting a substituted tetrahydro-4H-thiopyran-4-one of formula II with a hydroxylalkyl hydrazine having the formula VI $\quad H_2NNH-A-OH$ to form an intermediate having the formula

VII

An alcohol of formula VII can be reacted with an alkylsulfonyl or arylsulfonyl halide, preferably p-toluenesulfonyl halide, to yield a compound of the formula

VIII wherein Y is alkyl or aryl. The intermediate of formula VIII can be treated with a heterocyclic compound having the formula IX 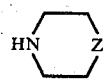

to yield the products of formula I.

The 5-oxide and 5,5-dioxide derivatives of a compound of formula I can, alternatively, be prepared by oxidizing the corresponding compound of formula I. Oxidation of a compound of formula I using one equivalent of sodium periodate or hydrogen peroxide yields the corresponding sulfoxide derivative. Oxidation of a compound of formula I using potassium permanganate or excess hydrogen peroxide yields the corresponding sulfonyl derivative. Alternatively, the sulfoxide and sulfonyl derivatives can be prepared by treating compounds of formula I with m-chloroperbenzoic acid. Treating a compound of formula I with an equivalent of m-chloroperbenzoic acid for from 2 to 24 hours at room temperature yields the corresponding sulfoxide derivative. Treating a compound of formula I, or a sulfoxide derivative of a compound of formula I, with two equivalents of m-chloroperbenzoic acid for 2 to 24 hours at room temperature (or for a shorter time with slight heating) yields the corresponding sulfonyl derivative.

The compounds of formula I form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide which are preferred, sulfate, nitrate, phosphate, borate, acetate, tartrate, maleate, citrate, succinate, benzoate, ascorbate, salicylate, methanesulfonate, benzenesulfonate, toluenesulfonate and the like.

The compounds of formula I, the pharmaceutically acceptable acid addition salts thereof, and the 5-oxide and 5,5-dioxide thereof, are useful in treating inflammation in mammalian species, e.g., rats, dogs, cats, monkeys, etc. Joint tenderness and stiffness (in conditions such as rheumatoid arthritis) are relieved by the above described compounds.

The compounds of this invention can be formulated for use as anti-inflammatory agents according to accepted pharmaceutical practice, in oral dosage forms such as tablets, capsules, elixirs, or powders, or in an injectable form in a sterile aqueous vehicle prepared according to conventional pharmaceutical practice. The compounds of this invention may be administered in amounts of 100 mg/70kg/day to 2 g/70kg/day, preferably 100 mg/70kg/day to 1 g/70kg/day.

The following examples are specific embodiments of this invention.

EXAMPLE 1

2,3,3a,4,6,7-Hexahydro-2-[3-(4-methyl-1-piperazinyl)propyl]-3-phenyl-7-(phenylmethylene)thiopyrano[4,3-c]pyrazole, maleate salt (1:2)

Tetrahydro-3,5-bis-(phenylmethylene)-4$\underline{H}$-thiopyran-4-one (5.3g) is refluxed with 3.4g of 3-(4-methyl-1-piperazinyl)propylhydrazine in a mixture of 40 ml of chloroform and 160 ml of methanol for 2 hours. The solvent is removed in vacuo to yield the free base of the title compound as a crude product.

The crude free base is dissolved in 50 ml of warm acetonitrile and treated with a warm solution of 4.5g of oxalic acid in 80 ml of acetonitrile. A precipitate forms almost immediately. The mixture is stirred at room temperature for 30 minutes and then cooled in an ice bath. The precipitate is collected by filtration and dried to yield 11g of crude 2,3,3a,4,6,7-hexahydro-2-[3-(4-methyl-1-piperazinyl)propyl]-3-phenyl-7-(phenylmethylene)thiopyrano[4,3-c]pyrazole, oxalate salt (1:2) melting point 202°–203° C.

The dioxalate salt is suspended in water and chloroform (100 ml of each) and treated with 9.9 g of potassium carbonate. The aqueous layer is separated and extracted with chloroform. The chloroform layers are combined and concentrated in vacuo to give the title compound as a free base.

The dimaleate salt of the title compound is prepared using the procedure described for the preparation of the dioxalate salt, and has a melting point of 179°–180° C.

EXAMPLE 2

2,3,3a,4,6,7-Hexahydro-2-[3-(4-methyl-1-piperazinyl)propyl]-3-phenyl-7-(phenylmethylene)thiopyrano[4,3-c]pyrazole A suspension of 4 g of the dimaleate salt of the title compound (prepared as described in Example 1) in water and chloroform (100 ml of each) is treated with 3.2 g of anhydrous potassium carbonate in portions. The aqueous layer is separated and washed with chloroform. The combined chloroform layers are dried using magnesium sulfate and concentrated in vacuo. The residue is crystallized from ether/hexane to give 1.8 g of the title compound melting point 90.5°–92.5° C.

EXAMPLE 3–14

By reacting the appropriate tetrahydro-3,5-bis-(phenylmethylene)-4$\underline{H}$-thiopyran-4-one with the appropriate heterocyclicalkylhydrazine, and where necessary treating the free base with the appropriate acid, the compound listed below is obtained

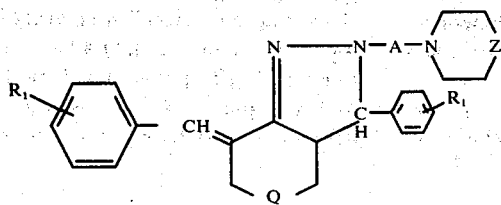

| Example | Q | R₁ | A | Z | salt | melting point |
|---|---|---|---|---|---|---|
| 3 | S | 4-methoxy | —(CH₂)₃— | N—CH₃ | dimaleate | 170.5–172° C |
| 4 | S | 4-methyl | —(CH₂)₃— | N—CH₃ | dimaleate | 174–176° C |
| 5 | S | 2-methyl | —(CH₂)₃— | N—CH₃ | dimaleate | 168.5–170° C |
| 6 | S | 4-methylsulfinyl | —(CH₂)₃— | N—CH₃ | dimaleate | 173–175° C |
| 7 | SO₂ | H | —(CH₂)₃— | N—CH₃ | dimaleate | 192–195° C |
| 8 | SO₂ | 4-methoxy | —(CH₂)₃— | N—CH₃ | dimaleate | 173.5–175° C |
| 9 | SO₂ | 2-methyl | —(CH₂)₃— | N—CH₃ | dimaleate | 165.5–167.5° C |
| 10 | SO | H | —(CH₂)₂— | N—H | | |
| 11 | S | 3-chloro | —(CH₂)₂— | N—phenyl | | |
| 12 | S | 2-trifluoromethyl | —(CH₂)₄— | N—CH₂—phenyl | | |
| 13 | S | 4-nitro | —(CH₂)₅— | CH₂ | | |
| 14 | S | 4-dimethylamino | —(CH₂)₃— | O | | |

What is claimed is:

1. A compound having the formula

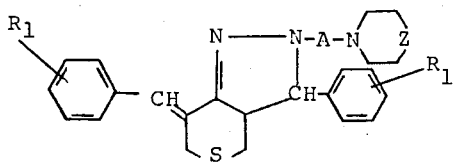

a pharmaceutically acceptable acid addition salt thereof, or a 5-oxide or 5,5-dioxide thereof, wherein A is a straight or branched chain alkylene group having 2 to 5 carbon atoms; R₁ is hydrogen, alkyl, alkoxy, trifluoromethyl, halogen, nitro, dialkylamino, or alkylsulfinyl; and Z is CH₂, oxygen or N—R₂, wherein R₂ is hydrogen, alkyl, aryl or arylalkyl; wherein aryl is phenyl or phenyl substituted with an alkyl, alkoxy, or halogen group, and wherein alkyl and alkoxy are groups having 1 to 8 carbon atoms.

2. A compound in accordance with claim 1 having the formula

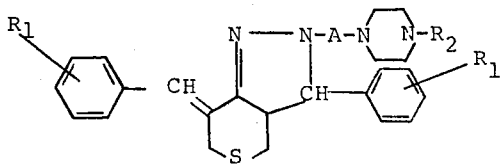

3. A compound in accordance with claim 2 wherein R₂ is alkyl.

4. A compound in accordance with claim 3 wherein R₂ is methyl.

5. A compound in accordance with claim 1 wherein R₁ is hydrogen, alkyl, alkoxy, or alkylsulfinyl.

6. The compound in accordance with claim 1 having the name 2,3,3a,4,6,7-hexahydro-2-[3-(4-methyl-1-piperazinyl)propyl]-3-phenyl-7-(phenylmethylene)thiopyrano[4,3-c]pyrazole, maleate salt (1:2).

7. The compound in accordance with claim 1 having the name 2,3,3a,4,6,7-hexahydro-2-[3-(4-methyl-1-piperazinyl)propyl]-3-phenyl-7-(phenylmethylene)thiopyrano[4,3-c]pyrazole.

8. The compound in accordance with claim 1 having the name 2,3,3a,4,6,7-hexahydro-3-(4-methoxyphenyl)-7-[(4-methoxyphenyl)methylene]-2-[3-(4-methyl-1-piperazinyl)propyl]thiopyrano[4,3-c]pyrazole, maleate salt (1:2).

9. The compound in accordance with claim 1 having the name 2,3,3a,4,6,7-hexahydro-3-(4-methylphenyl)-7-[(4-methylphenyl)methylene]-2-[3-(4-methyl-1-piperazinyl)propyl]thiopyrano[4,3-c]pyrazole, maleate salt (1:2).

10. The compound in accordance with claim 1 having the name 2,3,3a,4,6,7-hexahydro-3-(2-methylphenyl)-7-[(2-methylphenyl)methylene]-2-[3-(4-methyl-1-piperazinyl)propyl]thiopyrano[4,3-c]pyrazole, maleate salt (1:2).

11. The compound in accordance with claim 1 having the name 2,3,3a,4,6,7-hexahydro-2-[3-(4-methyl-1-piperazinyl)propyl]-3-[4-(methylsulfinyl)-phenyl]-7-[[4-(methylsulfinyl)phenyl]methylene]thiopyrano[4,3-c]pyrazole, maleate salt (1:2).

12. The compound in accordance with claim 1 having the name 2,3,3a,4,6,7-hexahydro-2-[3-(4-methyl-1-piperazinyl)propyl]-3-phenyl-7-(phenylmethylene)-thiopyrano[4,3-c]pyrazole,5,5-dioxide, maleate salt (1:2).

13. The compound in accordance with claim 1 having the name 2,3,3a,4,6,7-hexahydro-3-(4-methoxyphenyl)-7-[(4-methoxyphenyl)methylene]-2-[3-(4-methyl-1-piperazinyl)propyl]thiopyrano[4,3-c]pyrazole,5,5-dioxide, maleate salt (1:2).

14. The compound in accordance with claim 1 having the name 2,3,3a,4,6,7-hexahydro-3-(2-methylphenyl)-7-[(2-methylphenyl)methylene]-2-[3-(4-methyl-1-piperazinyl)propyl]thiopyrano[4,3-c]pyrazole,5,5-dioxide, maleate salt (1:2).

* * * * *